United States Patent [19]

Sugimoto et al.

[11] Patent Number: 5,523,307

[45] Date of Patent: * Jun. 4, 1996

[54] CYCLIC AMINE AND PHARMACOLOGICAL COMPOSITION

[75] Inventors: Hachiro Sugimoto, Ushiku; Takaharu Nakamura, Abiko; Norio Karibe; Isao Saito, both of Tsukuba; Kunizo Higurashi, Tokyo; Masahiro Yonaga; Takeru Kaneko, both of Tsukuba; Takahiro Nakazawa, Fujishiromachi; Masataka Ueno, Tsukuba; Kiyomi Yamatsu, Kamakura; Kohshi Ueno; Masuhiro Ikeda, both of Tsukuba, all of Japan

[73] Assignee: Eisai Co., Ltd., Tokyo, Japan

[*] Notice: The term of this patent shall not extend beyond the expiration date of Pat. No. 4,921,863.

[21] Appl. No.: 258,798

[22] Filed: Jun. 7, 1994

Related U.S. Application Data

[60] Continuation of Ser. No. 936,648, Aug. 28, 1992, abandoned, which is a division of Ser. No. 825,423, Jan. 24, 1992, Pat. No. 5,196,439, which is a continuation of Ser. No. 668,327, Mar. 14, 1991, abandoned, which is a continuation of Ser. No. 495,112, Mar. 19, 1990, abandoned, which is a continuation of Ser. No. 273,971, Nov. 21, 1988, abandoned.

[30] Foreign Application Priority Data

Nov. 27, 1987 [JP] Japan .................. 62-299438
Mar. 28, 1988 [JP] Japan .................. 63-74127

[51] Int. Cl.$^6$ .................. A61K 31/44; A61K 31/445; A61K 31/47

[52] U.S. Cl. .................. 514/314; 514/318; 514/319; 546/168; 546/174; 546/194; 546/205

[58] Field of Search .................. 546/168, 174, 546/194, 205; 514/314, 318, 319

[56] References Cited

U.S. PATENT DOCUMENTS 3,576,810  4/1971  Duncan et al. .................. 546/225
4,075,346  2/1978  Sasajima et al. .................. 424/267
4,101,662  7/1978  Ward et al. .................. 424/267
4,246,268  1/1981  Carr .................. 546/205
4,921,863  5/1990  Sugimoto et al. .................. 514/319

FOREIGN PATENT DOCUMENTS 2227868  11/1974  France .
61-227565  10/1986  Japan .
8802365  4/1988  WIPO .

OTHER PUBLICATIONS

Arzneimittelforschung, vol. 24, No. 4a, 1974, pp. 584–600; Hiltmann et al.
Journal Organic Chemistry, vol. 33, No. 9, 1968, pp. 3627–3632, Johnson.
Journal of Organic Chemistry, vol. 31, No. 10, 1966, pp. 3337–3342, Lynch et al.
Journal of Medicinal Chemistry, vol. 13, No. 1, 1970, pp. 1–6, Duncan et al.
Arzneimittelforschung, vol. 39, No. 4, 1989, pp. 445–450, Kaneko et al.
Japanese–United States Congress of Pharmaceutical Sciences, Dec. 2–7, 1987, p. 159, Karibe et al.
Chem. Abstract, CA (106) 213767Z, 1987, p. 645, Sugimoto et al.

*Primary Examiner*—Philip I. Datlow
*Attorney, Agent, or Firm*—Birch, Stewart, Kolasch & Birch

[57] ABSTRACT

A cyclic amine is defined by the formula:

$$A-X-N\diagup\diagdown B \atop \diagdown (CH_2)_n \diagup \qquad (I)$$

in which A is naphthyl, phenyl, quinolyl or alkyl, X is a group containing carbonyl, n is 2 or 3 and B is alkyl, halogen, phenyl or —YZ, Y being —O—, —CO— or —NH—, Z being phenyl, naphthyl, pyridyl, alkyl or cycloalkyl. It is useful to treat a mental symptoms associated with a cerebrovascular disease.

7 Claims, No Drawings

CYCLIC AMINE AND PHARMACOLOGICAL COMPOSITION

This application is a continuation of application Ser. No. 07/936,648 filed on Aug. 28, 1992, now abandoned, which is a Rule 60 divisional of Ser. No. 07/825,423 filed Jan. 24, 1992, now U.S. Pat. No. 5,196,439 which is a Rule 62 continuation of Ser. No. 07/668,327 filed Mar. 14, 1991, now abandoned which is a Rule 62 continuation of Ser. No. 07/495,112 filed Mar. 19, 1990, now abandoned which is a Rule 62 continuation of Ser. No. 07/273,971 filed Nov. 21, 1988 now abandoned.

The present invention relates to a novel cyclic amine derivative which exhibits an excellent activity as a pharmaceutical.

BACKGROUND OF THE INVENTION AND PRIOR ART

Various attempts have been made to treat cerebrovascular diseases with a drug. For example, cerebrovasodilators and cerebral metabolism activators are used. So far, however, there has been no drug which is very useful for the treatment of the cerebrovascular diseases. In particular, with respect to cerebrovascular dementia, mental dysfunction, etc. among various symptoms accompanying cerebrovascular diseases, no effective drug has yet been developed.

However, in recent years, a theory that an excitatory amino acid liberated after ischemia seriously participates in the death of nerve cells has attracted worldwide attention. This theory was substantiated by the facts that ischemia brings about liberation of a glutamate and the cell injury derived from ischemia is antagonized by a glutamate antagonist.

The present inventors have paid their attention to the neurotoxic activity of the above-described glutamate in starting the search for a new agent for treating cerebrovascular diseases, particularly an agent for improving a mental symptom accompanying the cerebrovascular diseases and have repeated studies on various compounds for a long period of time. As a result, we have found that a cyclic amine derivative which will be described hereinbelow exhibits an excellent activity on the suppression of glutamate liberation, which have led to the completion of the present invention.

Accordingly, an object of the present invention is to provide a cyclic amine derivative or pharmacologically acceptable salts thereof effective as an agent for improving mental symptoms accompanying cerebrovascular diseases, such as cerebral apoplexy, cerebral hemorrhage, cerebral infarction and cerebral arteriosclerosis, and polyinfarctive dementia, and a process for preparing said compound and pharmacologically acceptable salts thereof. Another object of the present invention is to provide a pharmaceutical comprising as an effective ingredient said compound or pharmacologically acceptable salts thereof.

SUMMARY OF THE INVENTION

The object compound of the present invention is a cyclic amine and pharmacologically acceptable salts thereof represented by the following formula (1):

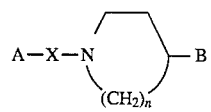
(I)

wherein A is a naphthyl group or a naphthyl group substituted with a lower alkoxy or hydroxy; phenyl group or a phenyl group substituted with a lower alkyl group or a halogen; a quinolyl group; or a lower alkyl group, n is an integer of 2 or 3, X is a group represented by the formula

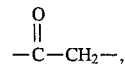

a group of the formula

a group represented by the formula

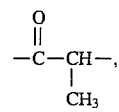

or a group represented by the formula

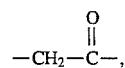

and

B is a lower alkyl group; a phenyl group which may be substituted with 1 to 3 of the same or different substituents selected from the group consisting of a halogen, a lower alkyl group, and a lower alkoxy group; or a group represented by the formula —Y—Z wherein Y is a group represented by the formula —O—, a group represented by the formula

or a group represented by the formula —NH— and

Z is a phenyl group which may be substituted with one or two same or different substituents selected from the group consisting of a halogen, a lower alkyl group, and a lower alkoxy group; a naphthyl group; a pyridyl group; a lower alkyl group; or a cycloalkyl group. The term "lower alkyl group" used in the above definition of A, B, and Z with respect to the compound (I) of the present invention is intended to mean a straight-chain or branched alkyl group having 1 to 6 carbon atoms, and examples thereof include methyl, ethyl, propyl, isopropyl, butyl, isobutyl, sec-butyl, tert- butyl, pentyl (amyl), isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethyl butyl, 1,1,2-trimethylpropyl, 1,2,2-trimethylpropyl, 1-ethyl-1-methylpropyl, and 1-ethyl-2-methylpropyl groups. Among them, methyl, ethyl, propyl, isopropyl groups etc. are preferable. A methyl group is most preferable.

n is intended to mean an integer of 2 or 3. When n is 2, the compound is a piperidine derivative. When n is 3, the compound is a homopiperidine derivative.

The term "lower alkoxy group" used in the definition of A, B, and Z is intended to mean an alkoxy group derived from the above-described lower alkyl group, and preferable examples thereof include methoxy, ethoxy, propoxy, isopropoxy, butoxy, and isobutoxy groups. Among them, a methoxy group is most preferable.

Examples of the halogen atom involved in the definition of A, B, and Z include chlorine, bromine, fluorine, and iodine.

The term "pharmacologically acceptable salt" is intended to mean a commonly used nontoxic salt, and examples thereof include those of inorganic acids, such as hydrochloride, hydrobromide, sulfate and phosphate, those of organic acids, such as acetate, maleate, tartrate, methanesulfonate, benzenesulfonate, and toluenesulfonate, and salts with amino acids such as arginine and aspartic acid.

In preferable embodiments of the cyclic amine and pharmacologically acceptable salts thereof as defined above, (1.) B is a lower alkyl; (2) B is —Y—Z in which Y is —O—; (3) A is a naphthyl group or a naphthyl group having a substituent of a lower alkyl or hydroxy, X is —CO—CH2—, n is 2 and B is —Y—Z in which Y is —O—, —CO— or —NH— and Z is phenyl or phenyl having one to three substituents, either the same as or different from each other, selected from the group consisting of a halogen, a lower alkyl, and a lower alkoxyl; or naphthyl; or (4) n is 2, B is a lower alkyl or —YZ and Z is defined as above however to exclude cycloalkyl.

The invention provides a process for preparing a cyclic amine or a pharmacologically acceptable salt thereof as defined above, which comprises the step of reacting a halide compound having the formula: A—X—Hal in which Hal is a halogen and A and X each are defined above, with a compound having the formula:

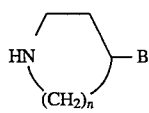   (III)

in which n and B each are defined above.

The invention also provides a pharmacological composition which comprises a pharmacologically effective amount of a cyclic amine or a pharmacologically acceptable salt thereof as defined above and a pharmacologically acceptable carrier and then a method for improving, treating or preventing a mental symptom associated with a cerebrovascular disease, which comprises administering a pharmacologically effective amount of a cyclic amine or a pharmacologically acceptable salt thereof as defined above to a subject suffering from the mental symptom associated with a cerebrovascular disease.

The compounds of the present invention may be prepared by various processes. A representative process for preparing the compounds of the present invention will now be described.

Process of preparation

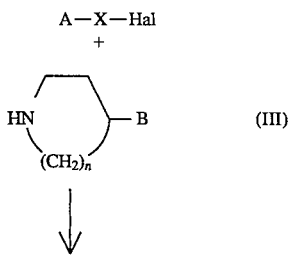

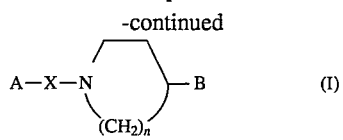

wherein A, X, B, and n are as defined above and Hal is a halogen atom.

Specifically, a halide represented by the general formula (II) is reacted with a compound represented by the general formula (III) to prepare a compound (I) which is an object compound of the present invention.

This reaction is a dehydrohalogenation conducted by any ordinary method while heating in the absence of any solvent or in an organic solvent which does not participate in the reaction, i.e., one selected from among alcoholic solvents, such as methanol, ethanol, and butanol, benzene, toluene, xylene, tetrahydrofuran, chloroform, carbon tetrachloride, and dimethylformamide. In this case, favorable results can be attained by conducting the reaction in the presence of an inorganic salt, such as sodium hydrogencarbonate, potassium carbonate, sodium carbonate or caustic soda, or an organic base such as triethylamine, pyridine, pyrimidine or diethylaniline.

The effect of the present invention will now be described in more detail with reference to the following pharmacological experiment.

Experimental Example

Glutamate liberation inhibitory activity in cerebral cortex slice

A male SD rat was decapitated, and cerebral cortices on both sides were then extirpated to prepare a slice having a thickness of 750 μm (weight: 10 to 20 mg) with a McIlwain tissue chopper. The slice was incubated in a Krebs-Henseleit liquid containing a test compound in the form of a solution thereof for 30 minutes. Then the slice was incubated in one ml of a Krebs-Henseleit liquid containing 50 mM of KCl and the test compound solution for 60 min. For control, a solvent was added to a Krebs-Henseleit liquid containing only SO mM of KCl.

The glutamate liberated in the solution was determined by HPLC, and the glutamate liberation inhibitory activity (%) in $10^{-4}$M of each test compound solution was calculated by the following equation:

$$\left(1 - \frac{\text{glutamate in each test compound solution}}{\text{amount of glutamate in control group}}\right) \times 100$$

TABLE 1

| glutamate liberation inhibitory activity | |
|---|---|
| test compound | glutamate liberation inhibitory activity (%) $1 \times 10^{-4}$M |
| compd. of Ex. 4 | 46 |
| compd. of Ex. 6 | 42 |
| compd. of Ex. 10 | 49 |
| compd. of Ex. 12 | 40 |
| compd. of Ex. 16 | 44 |
| compd. of Ex. 17 | 39 |
| compd. of Ex. 18 | 10 |
| compd. of Ex. 21 | 16 |

It is apparent from the above-described pharmacological experiment that the compounds of the present invention have a remarkable glutamate liberation inhibitory activity and exhibit a cell injury protective action and a learning disturbance improving action after ischemia based on this activity. Therefore, the compounds of the present invention exhibit a useful pharmacological action, particularly a remarkable ischemic cerebrovascular disease improving action for the central nervous system and are useful as an agent for improving, treating or preventing mental symptoms associated with cerebrovascular diseases such as cerebral apoplexy, cerebral hemorrhage, cerebral infarction, cerebral arteriosclerosis, and various types of dementia such as polyinfarcted dementia.

Further, the compounds of the present invention exhibited high safety in toxicity tests on rats. Therefore, the present invention is valuable from this viewpoint as well.

When the compounds of the present invention are used as a pharmaceutical for the above-described diseases, they may be orally or parenterally administered. The dose will vary depending on the severity of symptome, age, sex, weight and sensitivity of patients; method of administration; time and intervals of administration and properties, formulation, and kind of pharmaceutical preparations; kind of effective ingredients, etc., so that there is no particular limitation with respect to the dose. Normally, the compounds may be administered in a dose of about 0.1 to 300 mg, preferably about 1 to 100 mg, per day per adult, ordinarily in one to four portions.

The compounds of the present invention are converted into pharmaceutical preparations in the dosage form of, e.g., injections, suppositories, sublingual tablets, and capsules according to any method which is commonly accepted in the art.

In preparing injections, the effective ingredient is blended, if necessary, with a pH modifier, a buffer, a suspending agent, a solubilizing agent, a stabilizer, a tonicity agent, a preservative, etc., followed by preparation of an intravenous, subcutaneous, or intramuscular injection according to an ordinary method. In this case, if necessary, it is possible to lyophilize these preparations according to any ordinary method.

Examples of the suspending agent include methylcellulose, Polysorbate 80, hydroxyethylcellulose, gum arabic, powdered tragacanth, sodium carboxymethylcellulose, and polyoxyethylene sorbitan monolaurate.

Examples of the solubilizing agent include polyoxyethylene hydrogenated castor oil, Polysorbate 80, nicotinamide, polyoxyethylene sorbitan monolaurate, Macrogol, and ethyl esters of castor oil fatty acids.

Examples of the stabilizer include sodium sulfite, sodium metasulfite, and ether, and examples of the preservative include methyl p-hydroxybenzoate, ethyl p-hydroxybenzoate, sorbic acid, phenol, cresol, and chlorocresol.

EXAMPLES

Representative examples of the present invention will now be described for the purpose of aiding the understanding of the present invention. It is needless to say that the present invention will not be limited to these examples only.

EXAMPLE 1

2-(4Methylpideridinyl)-2'-acetonaphthone hydrochloride

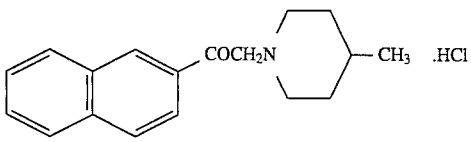

2.5 g of 2-bromo-2'-acetonaphthone, 1 g of methylpiperidine, 0.1 g of potassium iodide, and 3.1 g of triethylamine were added to 100 ml of ethanol. The mixture was refluxed for 20 min. The solvent was distilled off, and dichloromethane was added to the residue. The mixture was washed with water and dried. The dichloromethane was distilled off, and the residue was purified by column chromatography (silica gel) to prepare an oleaginous and oily intended compound. The compound was converted into a hydrochloride by an oridinary method and then recrystallized to prepare 1.87 g of an intended hydrochloride.

melting point: 202–203.5° C.

elementary analysis: $C_{18}H_{21}NO \cdot HCl$

|  | C | H | N |
|---|---|---|---|
| calculated (%): | 71.16 | 7.30 | 4.61 |
| found (%): | 71.21 | 7.59 | 4.50 |

EXAMPLE 2

2-[4-(p-Fluorobenzoyl)piperidinyl]-1'-methoxy-2'-acetonaphthone hydrochloride

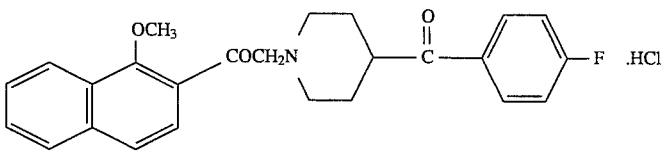

1.5 g of 2-bromo-1'-methoxy-2'-acetonaphthone, 1.3 g of 4-(p-fluorobenzoyl)piperidine hydrochloride, and 1.6 g of triethylamine were added to 60 ml of ethanol. The mixture was refluxed for 15 min. The solvent was distilled off, and dichloromethane was added to the residue. The mixture was washed with water and dried. The dichloromethane was distilled off, and the residue was purified by column chromatography (silica gel) to prepare an oleaginous intended compound. The compound was converted into a hydrochloride by an ordinary method and then recrystallized to prepare 1.38 g of an intended hydrochloride.

melting point: 195.5–196.2° C.

elementary analysis: $C_{25}H_{24}NO_3F \cdot HCl$

|  | C | H | N |
|---|---|---|---|
| calculated (%): | 67.95 | 5.70 | 3.17 |
| found (%): | 67.88 | 5.64 | 3.02 |

EXAMPLE 3

4-(p-Fluorobenzoyl)-1-(2'-naththoyl)piperidine

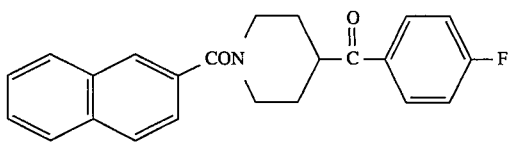

3.8 g of 2-naphthoyl chloride, 5.5 g of 4-(p-fluorobenzoyl)piperidine hydrochloride, and 5 g of triethylamine were added to 100 ml of tetrahydrofuran. The mixture was stirred at room temperature for 1 hr. The solvent was filtered off and then distilled off. Dichloromethane was added to the residue. The mixture was washed with water and dried. The dichloromethane was distilled off, and the residue was purified by column chromatography (silica gel) to prepare a crystal. The crystal was recrystallized to prepare 5 of an intended crystal.

melting point: 130.2–130.7° C.

elementary analysis: $C_{23}H_{20}NO_2F$

|  | C | H | N |
|---|---|---|---|
| calculated (%): | 76.44 | 5.78 | 3.88 |
| found (%): | 76.52 | 5.95 | 3.71 |

EXAMPLE 4

2-[4-(m-Nitrophenoxy)piperidinyl]-2'-acetonaphthone hydrochloride

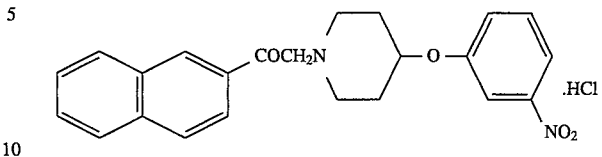

0.63 g of 2-bromo-2'-acetonaphthone, 0.65 g of 4-(m-nitrophenoxy)piperidine hydrochloride, and 1 g of triethylamine were added to 100 ml of ethanol. The mixture was refluxed for 30 min. The solvent was distilled off, and dichloromethane was added to the residue. The mixture was washed with water and dried. The dichloromethane was distilled off, and the residue was purified by column chromatography (silica gel) to prepare an oleaginous intended compound. The compound was converted into a hydrochloride by an ordinary method and then recrystallized to prepare 0.15 g of an intended hydrochloride.

melting point: 214–215° C.

elementary analysis: $C_{23}H_{22}N_2O_4 \cdot HCl$

|  | C | H | N |
|---|---|---|---|
| calculated (%): | 64.71 | 5.43 | 6.56 |
| found (%): | 64.57 | 5.34 | 6.52 |

EXAMPLES 5 to 25

Various compounds shown in Table 2 were synthesized in the same manner as that of Examples 1 to 4.

TABLE 2

| Ex. No. | structural formula | m.p. (°C.) | chemical formula | elem. anal. calcd. (%) found (%) | | |
|---|---|---|---|---|---|---|
|  |  |  |  | C | H | N |
| 5 | ![structure] | 125–126 | $C_{22}H_{22}N_2O_2 \cdot 2HCl$ | 63.01<br>62.90 | 5.77<br>5.52 | 6.68<br>6.83 |
| 6 | ![structure] | 201–201.5 | $C_{15}H_{21}NO_2 \cdot HCl$ | 68.77<br>69.01 | 6.68<br>6.79 | 4.22<br>4.19 |
| 7 | ![structure] | 206.5–207 | $C_{21}H_{22}NO_2F \cdot HCl$ | 67.11<br>67.23 | 6.17<br>6.46 | 3.73<br>3.62 |
| 8 | ![structure] | 205–205.5 | $C_{15}H_{15}NO_2F \cdot HCl$ | 60.10<br>60.35 | 6.39<br>6.27 | 4.67<br>4.67 |

TABLE 2-continued

| Ex. No. | structural formula | m.p. (°C.) | chemical formula | elem. anal. calcd. (%) found (%) | | |
|---|---|---|---|---|---|---|
| | | | | C | H | N |
| 9 | 3-Cl-C$_6$H$_4$-CO-CH$_2$-N(piperidine-4-CO-C$_6$H$_4$-4-F)·HCl | 237~238 | C$_{20}$H$_{15}$NO$_2$ClF·HCl | 60.46<br>60.60 | 5.33<br>5.32 | 3.53<br>3.48 |
| 10 | naphthyl-2-CO-CH$_2$-N(piperidine-4-O-C$_6$H$_4$-4-F)·HCl | 224.5~225 | C$_{23}$H$_{22}$NO$_2$·HCl | 69.08<br>68.95 | 5.80<br>5.76 | 3.50<br>3.26 |
| 11 | 6-CH$_3$O-naphthyl-2-CO-CH$_2$-N(piperidine-4-CO-C$_6$H$_4$-4-F)·HCl | 240.8~241.2 | C$_{25}$H$_{24}$NO$_3$F·HCl | 67.95<br>68.05 | 5.70<br>5.71 | 3.17<br>3.06 |
| 12 | 3-CH$_3$-naphthyl-2-CO-CH$_2$-N(piperidine-4-CO-C$_6$H$_4$-4-F)·HCl | 244.5~246 | C$_{25}$H$_{24}$NO$_2$F·HCl | 70.50<br>70.47 | 5.92<br>5.80 | 3.29<br>3.35 |
| 13 | quinolin-3-CO-CH$_2$-N(piperidine-4-CO-C$_6$H$_4$-4-F)·2HCl·H$_2$O | 247.5~248 | C$_{23}$H$_{21}$N$_2$O$_2$F·2HCl·H$_2$O | 59.11<br>59.16 | 5.39<br>5.35 | 5.99<br>5.78 |
| 14 | naphthyl-2-CO-CH(CH$_3$)-N(piperidine-4-CO-C$_6$H$_4$-4-F)·HCl | 225.5~227 | C$_{25}$H$_{24}$NO$_2$F·HCl | 70.50<br>70.43 | 5.92<br>6.05 | 3.29<br>3.12 |
| 15 | naphthyl-2-CO-CH$_2$-N(piperidine-4-CO-C$_6$H$_3$-3,4-F$_2$)·HCl | 245~246 | C$_{24}$H$_{23}$NO$_2$F$_2$·HCl | 67.05<br>67.31 | 5.16<br>5.36 | 3.26<br>3.16 |
| 16 | naphthyl-2-CO-CH$_2$-N(piperidine-4-CO-C$_6$H$_4$-3-F)·HCl | 235.5~236 | C$_{24}$H$_{22}$NO$_2$F·HCl | 69.98<br>69.44 | 5.63<br>5.65 | 3.40<br>3.27 |
| 17 | naphthyl-2-CO-CH$_2$-N(piperidine-4-CO-C$_6$H$_2$-2,4,6-(OCH$_3$)$_3$)·HCl | 176.5~178 | C$_{27}$H$_{25}$NO$_5$·HCl | 67.00<br>67.21 | 6.25<br>6.18 | 2.89<br>2.78 |

TABLE 2-continued

| Ex. No. | structural formula | m.p. (°C.) | chemical formula | elem. anal. calcd. (%) found (%) | | |
|---|---|---|---|---|---|---|
| | | | | C | H | N |
| 18 | (2-naphthyl-CO-CH$_2$-N(piperidine-4-yl-CO-1-naphthyl)) ·HCl | 240–240.5 | C$_{28}$H$_{25}$NO$_2$·HCl | 75.75 75.63 | 5.90 6.05 | 3.15 3.11 |
| 19 | (2-naphthyl-CH$_2$-CO-N(piperidine-4-yl-CO-C$_6$H$_4$-4-F)) | 117–118 | C$_{24}$H$_{22}$NO$_2$F | 76.78 76.82 | 5.91 6.17 | 3.73 3.53 |
| 20 | (2-naphthyl-CO-CH$_2$-N(piperidine-4-yl-C$_6$H$_4$-4-F))·HCl | 246.5–248 | C$_{23}$H$_{22}$NOF·HCl | 71.96 72.31 | 6.04 6.13 | 3.65 3.58 |
| 21 | (2-naphthyl-CO-CH$_2$-N(piperidine-4-yl-O-C$_6$H$_4$-4-CO-CH$_3$))·HCl | 224.5–226 | C$_{25}$H$_{25}$NO$_3$·HCl | 70.83 71.02 | 6.18 6.21 | 3.30 3.34 |
| 22 | (2-naphthyl-CO-CH$_2$-N(piperidine-4-yl-CO-C$_6$H$_4$-4-CO-CH$_3$))·HCl | 224.5–225.5 | C$_{26}$H$_{25}$NO$_3$·HCl | 71.63 71.71 | 6.01 6.02 | 3.21 3.33 |
| 23 | (2-naphthyl-CO-CH$_2$-N(piperidine-4-yl-CO-cyclohexyl))·HCl | 223–244 | C$_{24}$H$_{23}$NO$_2$·HCl | 72.07 71.99 | 7.56 7.52 | 3.50 3.44 |
| 24 | (2-naphthyl-CO-CH$_2$-N(piperidine-4-yl-NH-C$_6$H$_4$-4-F))·2HCl | 253.5–254 | C$_{24}$H$_{23}$N$_2$OF·2HCl | 63.45 63.17 | 5.79 5.65 | 6.43 6.20 |
| 25 | (2-naphthyl-CO-CH$_2$-N(homopiperidine-CO-C$_6$H$_4$-4-F))·HCl | 207–207.5 (dec.) | C$_{25}$H$_{24}$NO$_2$F·HCl | 70.50 70.53 | 5.91 5.80 | 3.29 3.36 |
| 26 | (1-hydroxy-2-naphthyl-CO-CH$_2$-N(piperidine-4-yl-CO-C$_6$H$_4$-4-F)) | 236–237.5 | C$_{24}$H$_{22}$NO$_3$F | 67.21 67.05 | 5.64 5.44 | 3.27 3.13 |

We claim:

1. A method for improving, treating or preventing a mental symptom associated with a cerebrovascular disease due to ischemia and elevated glutamate levels which comprises administering a pharmacologically effective amount of a cyclic amine or a pharmaceutically acceptable salt thereof represented by the formula:

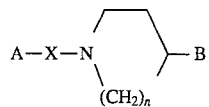

wherein A is an unsubstituted naphthyl group or a naphthyl group substituted with a lower alkoxy group, phenyl or a phenyl group substituted with a lower alkyl group or halogen, or a quinolyl group, n is 2, X is a group represented by the formula

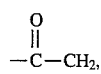

a group of the formula

a group represented by the formula

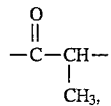

or a group represented by the formula

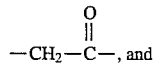

B is a group represented by the formula —Y—Z wherein
Y is a group represented by the formula

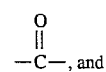

Z is a phenyl group which may be substituted with one or two identical or different substituents selected from the group consisting of halogen, lower alkyl and lower alkoxy; a pyridyl group; or a lower alkyl group, to a patient suffering from the mental symptom associated with a cerebrovascular disease due to ischemia and elevated glutamate levels.

2. A method according to claim 1, wherein A is a naphthyl group or a naphthyl group substituted with a lower alkoxy group, X is

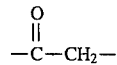

and Z is phenyl which may be substituted with one or two identical or different substituents selected from the group consisting of halogen, lower alkyl and lower alkoxy.

3. A method according to claim 1, wherein Z is phenyl substituted with one substituent.

4. A method according to claim 3, wherein Z is phenyl substituted with halogen.

5. A method according to claim 4, wherein said halogen is fluorine.

6. A method according to claim 1, wherein A is an unsubstituted naphthyl group.

7. A method according to claim 1, wherein the cyclic amine salt is 4-acetylpiperidinyl-1-(2'-acetonaphthone) hydrochloride, 2-(4-(p-fluorobenzoyl)piperidinyl)-3'-methyl-2'-acetonaphthone hydrochloride, 2-(4-(m-fluorobenzoyl)piperidinyl)-2'-acetonaphthone hydrochloride or 2-(4-(2,4,6-trimethoxybenzoyl)piperidinyl)-2'-acetonaphthone hydrochloride.

* * * * *

UNITED STATES PATENT AND TRADEMARK OFFICE
CERTIFICATE OF CORRECTION

PATENT NO. : 5,523,307
DATED : June 4, 1996
INVENTOR(S) : Sugimoto et al.

It is certified that error appears in the above-indentified patent and that said Letters Patent is hereby corrected as shown below:

Title page, item "[21] Appl. No.", please change the application number from "258,798" to properly read --255,798--.

Signed and Sealed this

Seventeenth Day of December, 1996

Attest:

BRUCE LEHMAN

*Attesting Officer*  *Commissioner of Patents and Trademarks*